United States Patent [19]

Webler et al.

[11] Patent Number: 4,595,012
[45] Date of Patent: Jun. 17, 1986

[54] LUMEN MOUNTED ELECTRODES FOR PACING AND INTRA-CARDIAC ECG SENSING

[75] Inventors: William E. Webler, Santa Ana; Clement Lieber, Yorba Linda, both of Calif.

[73] Assignee: American Hospital Supply Corporation, Evanston, Ill.

[21] Appl. No.: 570,632

[22] Filed: Jan. 13, 1984

[51] Int. Cl.$^4$ .......................... A61B 5/04; A61N 1/05
[52] U.S. Cl. ..................................... 128/642; 128/786
[58] Field of Search .................. 128/642, 784–786, 128/419 P, 693

[56] References Cited

U.S. PATENT DOCUMENTS

| 3,664,347 | 5/1972 | Harmjanz | 128/786 |
| 3,866,615 | 2/1975 | Hewson | 128/784 X |
| 3,935,864 | 2/1976 | Lagergren | 128/786 |
| 3,949,757 | 4/1976 | Sabel | 128/786 |
| 3,995,623 | 12/1976 | Blake et al. | 128/642 |
| 4,161,952 | 7/1979 | Kinney et al. | 128/786 |
| 4,172,451 | 10/1979 | Kline | 128/642 |
| 4,217,910 | 8/1980 | Khalil | 128/670 |
| 4,328,806 | 5/1982 | Cooper | 128/642 |
| 4,328,812 | 5/1982 | Ufford et al. | 128/786 |
| 4,380,237 | 4/1983 | Newbower | 128/693 |
| 4,402,328 | 9/1983 | Doring | 128/785 |
| 4,481,953 | 11/1984 | Gold et al. | 128/786 |

OTHER PUBLICATIONS

Mindt et al., "Stimulating Electrode . . . ", Med. & Biol. Eng., Sep. 1973, vol. 11, No. 5, pp. 659–660.

Primary Examiner—Lee S. Cohen
Attorney, Agent, or Firm—Gordon L. Peterson

[57] ABSTRACT

An apparatus for making electrical contact within the heart of a patient for pacing the heart and ECG sensing comprising an elongated tube sized to be received through a vein or artery into the heart and having a peripheral wall, at least one lumen and an opening in the peripheral wall which extends from the lumen to the exterior of the tube. An electrode is mounted in the lumen with the electrode being exposed at the opening. At least one conductive lead is coupled to the electrode and extends proximally within the tube. The tube has a body line, and the electrode extends radially outwardly no farther than the body line.

16 Claims, 7 Drawing Figures

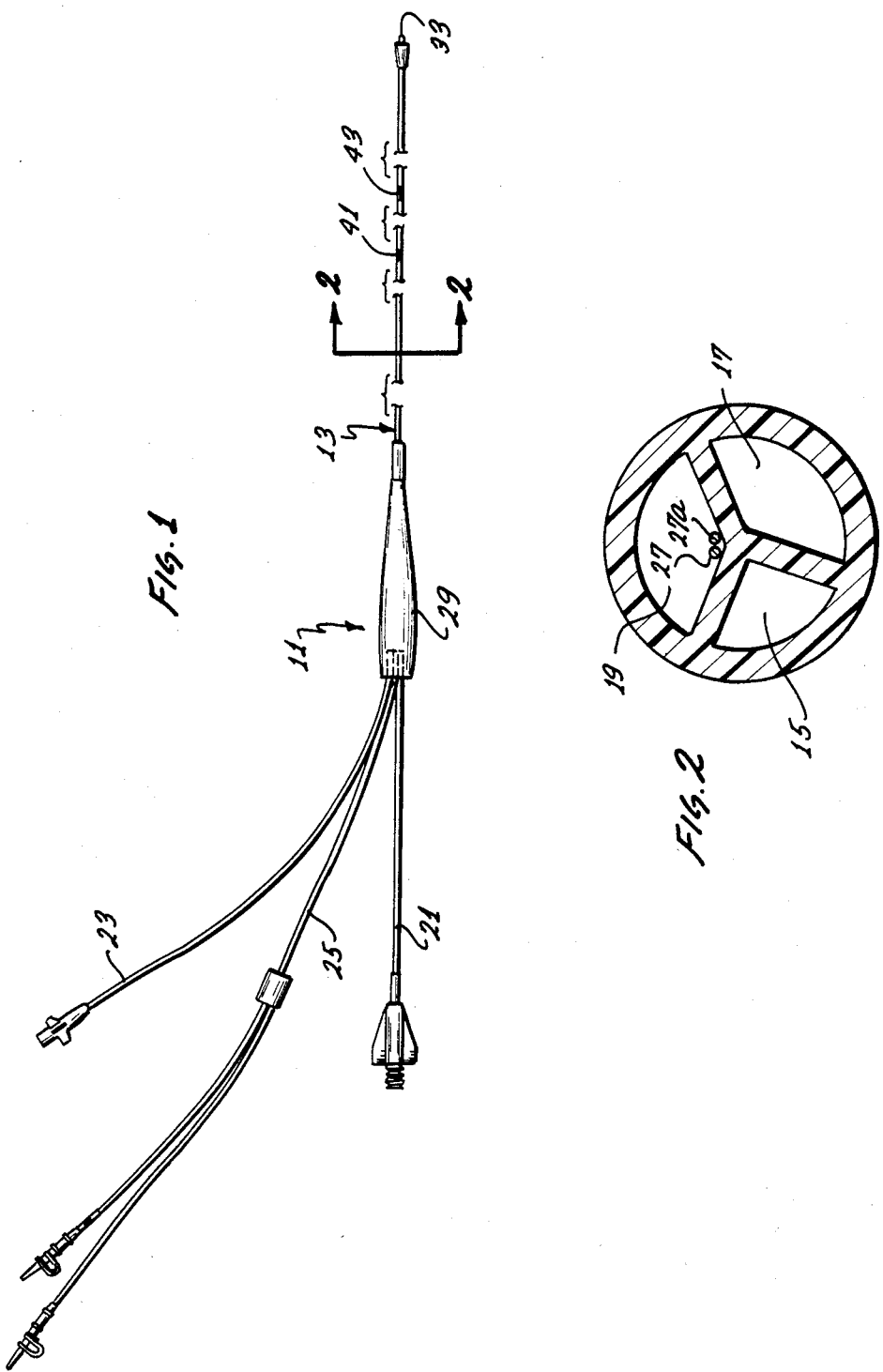

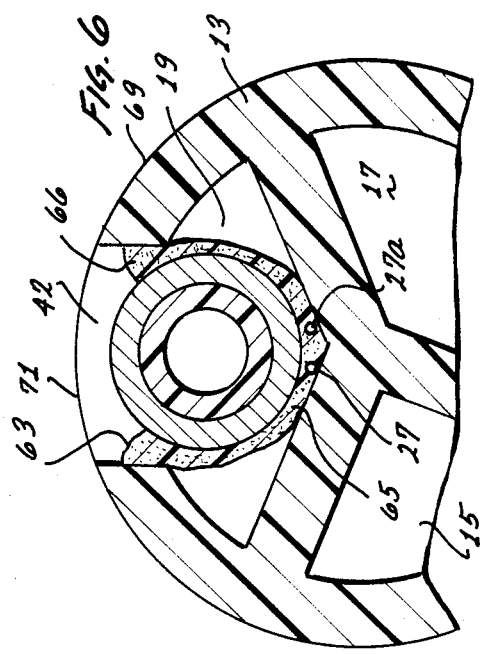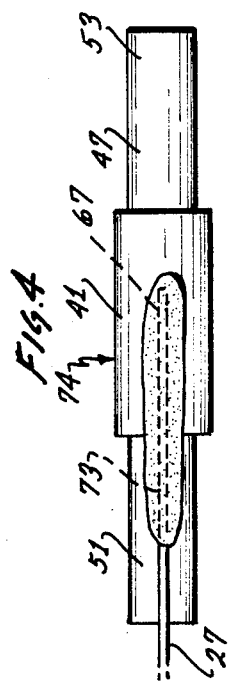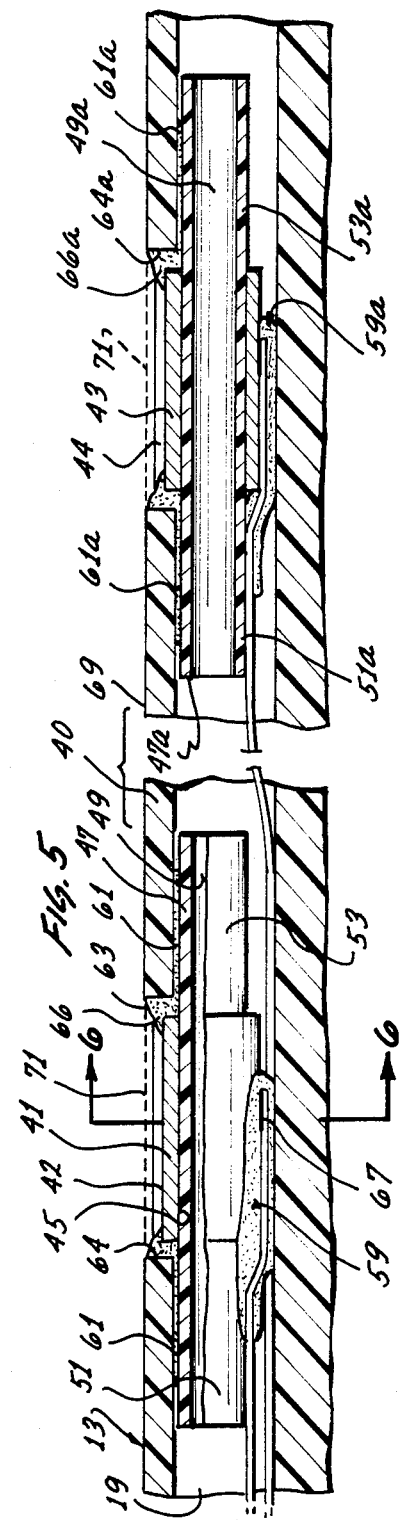

LUMEN MOUNTED ELECTRODES FOR PACING AND INTRA-CARDIAC ECG SENSING

BACKGROUND OF THE INVENTION

Various medical procedures require the making of electrical contact with specified regions within the heart. For example, in an intra-cardial ECG (electrocardiogram), an apparatus, such as a catheter or probe, is inserted through a vein or an artery into the appropriate location within the heart. The apparatus has one or more electrodes which are placed in close proximity to the tissue of the heart so that the electrical activity within the heart can be appropriately monitored. Intra-cardial ECG sensing can be done, for example, when the apparatus is within the heart for other purposes.

Similarly, temporary pacing of the heart also requires the making of electrical contact between one or more electrodes of an apparatus, such as a probe or catheter, and the tissue of the heart. For example, during certain surgery, a catheter may be inserted into the heart to monitor various cardiovascular functions. Such a catheter may be equipped with appropriate pacing electrodes so that, if the patient should suffer a cardiac arrest, the heart can be quickly given the necessary electrical therapy.

It is conventional practice to mount the electrodes on the exterior surface of the probe or catheter, and constructions of this type are shown, for example, in Blake et al U.S. Pat. No. 3,995,623 and Khalil U.S. Pat. No. 4,217,910. Unfortunately, there is a danger that electrodes mounted on the exterior of the probe or catheter may become loose and slide off the probe or catheter and remain in the patient. This can occur, for example, as the result of sliding of the catheter through a tubular introducer which is used in placement of the catheter. In addition, an electrode mounted on the exterior surface of the probe or catheter tends to project radially beyond the catheter body line and, as such, is more likely to be slid off of the catheter as a result of relative movement between the catheter and the introducer.

SUMMARY OF THE INVENTION

This invention greatly reduces the risk of inadvertent removal of the electrode. This is accomplished by mounting the electrode within a lumen of the apparatus and by mounting the mounting means for the electrode at least partially within the lumen. To make demounting of the electrode even less likely and to reduce the likelihood of the electrode forming an impediment to movement of the apparatus, the electrode and the mounting means therefor preferably lie radially inwardly of the body line of the apparatus.

This invention is applicable to an apparatus, such as a probe or a catheter, which includes an elongated tube sized to be received through a vein or an artery into the heart and having proximal and distal ends, a peripheral wall, at least one lumen extending longitudinally within the tube, and an opening in the peripheral wall which extends from the lumen to the exterior of the tube. The apparatus also includes an electrode and means at least partially within the lumen for mounting the electrode within the lumen with the electrode being exposed at the opening. At least one conductive lead is coupled to the electrode and extends from the electrode within the tube. Of course, the apparatus may include any desired number of the electrodes.

The tube has a body line, and the electrode preferably extends radially outwardly no farther than the body line. Although various different constructions are possible, the electrode preferably includes a conductive member with a generally axial passage, and the mounting means includes a mounting member in the lumen which extends into the passage to thereby mechanically interlock the mounting member and the conductive member. At least a portion of the mounting member is in the lumen and displaced axially of the opening to form a mechanical interlock with the tube. Thus, this structure at least assists in mechanically locking the conductive member in the lumen.

The electrode and the mounting member form an electrode assembly, and to facilitate insertion of this assembly into the lumen through the opening, the mounting member is preferably resiliently bendable. This characteristic can be enhanced by making the mounting member tubular. However, a stiff mounting member can be used, if desired. In this event, the electrode is inserted through the opening, and subsequently, the tube is bent to allow the relatively stiff mounting member to be inserted through the opening into the lumen and through the electrode.

To further assist in locking the electrode assembly within the lumen, the mounting means preferably includes an insulating adhesive for bonding the mounting member and the conductive member together and for bonding them to the tube. The lead is welded to the electrode and extends through the insulating adhesive. The electrode is preferably positioned within the lumen so that the weld is in the lumen and faces generally away from the opening.

This invention can be employed in a single or multiple lumen apparatus. For example, the apparatus may include a catheter tube with a balloon, a balloon inflation lumen, and one or more other lumens, such as a through lumen for providing various useful medical functions within the heart.

The invention, together with additional features and advantages thereof, may best be understood by reference to the following description taken in connection with the accompanying illustrative drawings.

BRIEF DESCRIPTION OF THE DRAWINGS

FIG. 1 is an elevational view of a catheter, with portions broken away, constructed in accordance with the teachings of this invention.

FIG. 2 is an enlarged, sectional view taken generally along line 2—2 of FIG. 1.

FIG. 4 is a plan view showing the electrode assembly prior to its insertion into the lumen.

FIG. 5 is an axial, sectional view through the portions of the catheter which include the electrodes.

FIG. 6 is a sectional view taken generally along line 6—6 of FIG. 5.

DESCRIPTION OF THE PREFERRED EMBODIMENT

Figure 3:
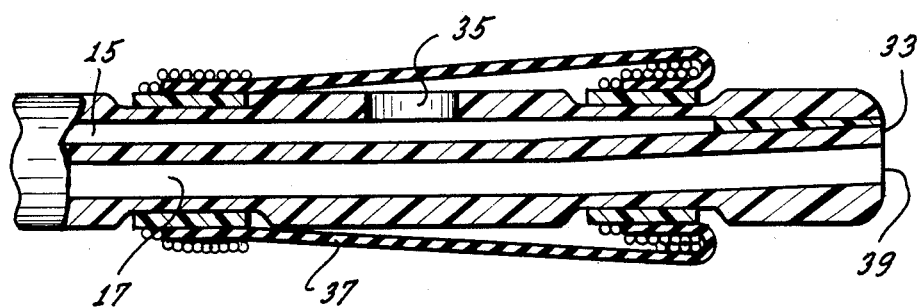
FIG. 3 is a fragmentary, axial, sectional view showing the distal tip of the catheter.

FIG. 1 shows an apparatus in the form of a catheter 11 which comprises an elongated catheter tube 13 having a balloon inflation lumen 15 (FIG. 2), a through lumen 17 and an electrode lumen 19. A pressure monitoring tube 21 and a balloon inflation tube 23 are fused to the tube 13 within the through lumen 17 and the balloon inflation lumen 15, respectively. A conduit 25 for insulated electrode leads 27 and 27a (FIG. 2) is fused to the tube 13 within the electrode lumen 19. The proximal end of the catheter tube 13 and the distal ends of the tubes 21 and 23 and the conduit 25 are encased by a flexible sleeve 29.

The catheter tube 13 may be extruded from a suitable biocompatible plastic material. The catheter tube 13 is flexible, elongated and sized to be received through a vein or an artery into the heart. The catheter tube 13 has a proximal end within the sleeve 29 and a distal end 33.

The balloon inflation lumen 15 extends continuously from the proximal end of the tube 13 through a port 35 (FIG. 3) to a balloon 37 closely adjacent the distal end 33. The balloon 37 and the manner in which it is inflated through the balloon inflation lumen 15 are conventional.

The through lumen 17 extends continuously from the proximal end of the tube 13 to the distal end 33 where it opens at a distal port 39 (FIG. 3). The through lumen 17 can be used, for example, to monitor pressures within the patient.

The catheter 11 includes a proximal electrode 41 and a distal electrode 43 both of which are mounted within the electrode lumen 19. The electrode lumen 19 extends continuously from the proximal end of the tube 13 to a location distally of the distal electrode 43. For example, the proximal electrode may be 9.35 to 9.65 inches from the distal end 33, and the distal electrode 43 may be 6.2 to 6.4 inches from the distal end 33. Of course, the catheter 11 can be provided with additional lumens, if desired, to provide additional functions for the catheter.

FIGS. 5 and 6 show how the electrodes 41 and 43 are mounted in the electrode lumen 19. In this embodiment, the electrodes 41 and 43 and their mounting are identical, and accordingly, portions of the mounting structure for the distal electrode corresponding to portions of the mounting structure for the proximal electrode are designated by corresponding reference numerals followed by the letter "a."

The electrodes 41 and 43 are identical, and each of them, in the illustrated embodiment, is in the form of a tubular conductive member or sleeve of a suitable conductive biocompatible metal, such as stainless steel. The catheter tube 13 has a peripheral wall 40 (FIG. 5) with openings 42 and 44 (FIG. 6) for exposing portions of the electrodes 41 and 43, respectively. The electrode 41 has a cylindrical, axial passage 45 extending completely through it and, although various configurations can be used, the electrode 41 is cylindrical.

The mounting means for the electrode 41 includes a tubular, resiliently bendable mounting member 47 of a suitable nontoxic material, such as PVC. Although various different configurations can be used, the mounting member 47 is cylindrical and forms a sliding fit with the passage 45 and it has a cylindrical, axial passage 49 extending completely through it. The mounting member 47 extends completely through the electrode 41 and has end portions 51 and 53 in the lumen 19 on opposite sides of the electrode. As shown in FIG. 5, the end portions 51 and 53 form a mechanical interlock with the catheter tube 13 on opposite sides of the opening 42.

The mounting means also includes an insulating adhesive 59, such as urethane, which bonds the electrode 41 to the mounting member 47 and bonds both of these members within the lumen 19 and to the catheter tube 13. Preferably, the insulating adhesive includes sleeve sections 61 which encase regions of the end portions 51 and 53, respectively, and bond the end portions to the confronting surfaces of the lumen 19. In addition, the adhesive 59 preferably includes radial sections 63 which bond the periphery of the opening 42 to the adjacent surfaces of the electrode 41, including end faces 64 of the tube and a portion of the outer periphery. A flange section 66 overlies a region of the electrode 41 along the full length of the periphery of the opening 42. The radial sections also tend to get between the confronting surfaces of the passage 45 and the exterior surface of the mounting member 47 to bond these two members together. The adhesive 59 includes a dished section 65 (FIG. 6) that bonds the radial inner regions of the electrode 41 to the adjacent surfaces of the lumen 19. In addition, the dished sections 65 partially circumscribe the electrode 41 to tend to retain it securely in position.

The lead 27 has its insulation stripped away at one end, and the electrode 41 is coupled to the lead 27 by a spot weld 67 at such end of the lead. The lead 27 extends through the adhesive 59, the lumen 19 and the conduit 25 to appropriate electronic equipment (not shown). The spot weld 67 and the lead 27 are in the lumen 19 and face generally away from the opening 42. In the embodiment illustrated, they are displaced nearly 180 degrees from the center of the opening 42 and, by keeping them away from the opening, they do not reduce the exposed surface area of the electrode 41 and they are not subject to handling or contact of the type that would tend to weaken or separate the joint between them.

As shown in FIG. 5, the axial dimension of the electrode 41 is only slightly less than the axial dimension of the opening 42. The circumferential extent of the opening 42 can vary depending upon the desired exposure of the electrode 41. By exposing only a segment of the periphery of the electrode 41, the current density at such electrode is increased to the extent that physical contact between the electrode and heart tissue, when the catheter 11 is used for pacing, may not be required.

The peripheral wall 40 has an outer peripheral surface 69, and the outline of that surface over the opening 42 is a body line 71 of the tube 13. The electrode 41 extends radially outwardly no farther than about the body line 71, and in the embodiment illustrated, lies slightly radially inwardly of the body line. Thus, the electrode 41 does not extend out of the lumen 19 and the opening 42. In addition, the mounting member 47 does not extend out of the lumen 19, and the insulating adhesive 59 extends radially outwardly no farther than the body line 71.

In construction of the catheter 11, the lead 27 is welded to the electrode 41 and the weld 67, a length of the lead 27 extending from the weld, and adjacent regions of the electrode and mounting member 47 are covered with a strip 73 (FIG. 4) of a suitable insulating adhesive material, such as urethane. This provides strain relief for the lead 27 and the weld 67, insulates the portions of the lead and weld that are covered, and bonds the mounting member 47 to the electrode 41. The construction shown in FIG. 4 forms an electrode assembly 74.

Next, the leads 27 are run through the opening 42 and proximally through the lumen 19. Then the opening 42 and the adjacent regions of the lumen 19 are enlarged by inserting an expander (not shown) through the opening and into the lumen to resiliently expand the plastic material of the catheter tube 13. The end portion 51 is then inserted through the opening 42 and into the lumen, and the mounting member 47 is resiliently bent until the free end of the end portion 53 can pass through the opening into the lumen 19. The electrode assembly 74 is then adjusted longitudinally to position the electrode in the opening 42 as shown in FIG. 5. The insertion process described above is carried out with the weld 67 facing away from the opening 42. The plastic material of the catheter tube 13 has sufficient memory to recover from the deformation it underwent during the assembly process. Finally, the insulating adhesive in a flowable, curable state is applied through the gap between the electrode 41 and the periphery of the opening 42 and allowed to run along the surfaces of the electrode and mounting member to form the sections 61, 63, 65 and 66 as described above.

Figure 7:
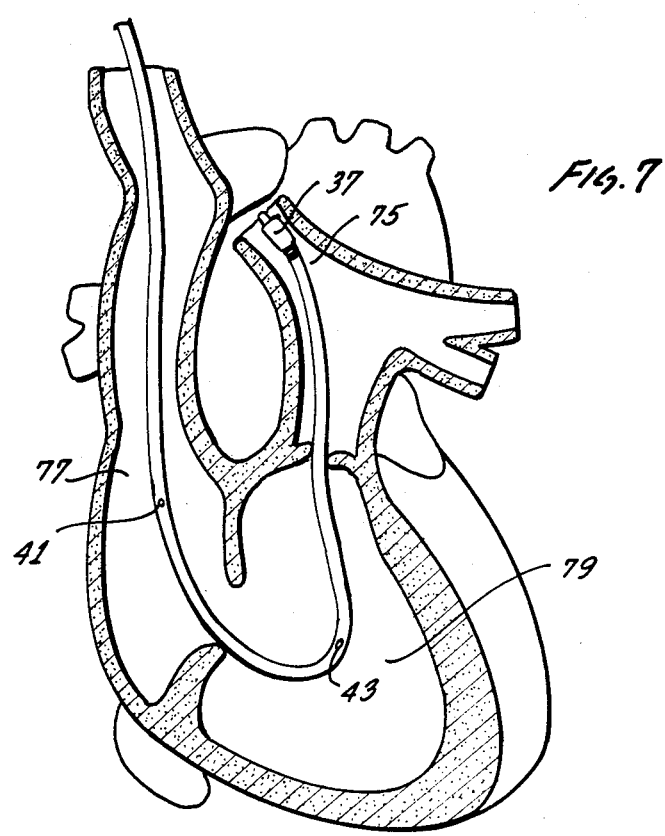
FIG. 7 is a sectional view of the human heart showing one example of how the apparatus of this invention can be used.

In use of the catheter 11, the catheter tube 13 is introduced through a vein or an artery of a patient and into the heart (FIG. 7) using known techniques. The balloon 37 is inflated through the balloon inflation lumen 15 and the port 35, and the inflated balloon is used to carry the distal end 33 of the catheter 11 to the desired location. In the example shown in FIG. 7, the balloon 37 is carried into the pulmonary artery 75. Because the electrodes 41 and 43 are mounted in the electrode lumen 19 below the body line 71, they will not rub against any introducer which is used, either during the insertion or withdrawal of the catheter tube 13.

The location of the catheter tube 13 within the heart will, of course, depend upon the procedure being carried out. For example, for intra-cardial ECG, the catheter tube 13 is inserted into the heart to place the electrodes 41 and 43 in the superior vena cava 77 and the right ventricle 79, respectively. The electrodes 41 and 43 are in proximity to the heart tissue across the appropriate portion of the heart's electrical field so that they can sense the electrical activity within the heart in a known manner. For pacing, the electrodes 41 and 43 may be similarly located. The catheter tube 13 may be placed within the heart solely for intra-cardial ECG sensing or temporary pacing or for other purposes, such as monitoring of the cardiovascular system.

Although an exemplary embodiment of the invention has been shown and described, many changes, modifications and substitutions may be made by one having ordinary skill in the art without necessarily departing from the spirit and scope of this invention.

We claim

1. An apparatus for making electrical contact within the heart of a patient comprising:
an elongated tube sized to pass through a vein or an artery and into the heart, said tube having proximal and distal ends, a peripheral wall, at least one lumen extending longitudinally within the tube and an opening in the peripheral wall which extends from the lumen to the exterior of the tube;
an electrode including a conductive member with a generally axial passage;
means at least partially within the lumen for mounting the electrode within said lumen with the electrode being exposed at said opening, said mounting means including a mounting member in said lumen, at least a portion of said mounting member being in said passage, extending into said lumen and being displaced axially of the opening to at least assist in mechanically locking the conductive member in the lumen;
at least one conductive lead coupled to said electrode and extending from said electrode within said tube; and
said peripheral wall having an outer peripheral surface which extends along a major length of said tube with the outline of said peripheral surface over said opening forming a body line and said electrode extends radially outwardly no farther than said body line whereby said apparatus is no larger radially at the electrode than at regions lying axially of the electrode and the mounting means.

2. An apparatus as defined in claim 1 wherein said passage extends through said electrode and said mounting means extends through said passage and has end portions outside said passage on opposite sides of the conductive member.

3. An apparatus as defined in claim 1 wherein said mounting member is resiliently bendable.

4. An apparatus as defined in claim 1 wherein said mounting member is tubular.

5. An apparatus as defined in claim 1 wherein said mounting member includes an insulating adhesive to at least assist in holding the mounting member and the conductive member together.

6. An apparatus as defined in claim 5 wherein said lead extends at least partially through the insulating adhesive and is welded to the electrode and the weld is in said lumen and faces generally away from the opening.

7. An apparatus as defined in claim 1 wherein said one lumen is a first lumen and said tube has a second lumen and a third lumen and said apparatus includes an inflatable balloon adjacent the distal end of the tube, said second lumen extends to the balloon to provide for balloon inflation and said third lumen is a through lumen and extends at least substantially to the distal end and opens at a distal port.

8. An apparatus as defined in claim 1 wherein said electrode is a first electrode and said opening is a first opening, said tube has a second opening in the peripheral wall which extends from the lumen to the exterior of the tube and said apparatus includes a second electrode mounted within the lumen with the second electrode exposed at the second opening and at least a second conductive lead coupled to the second electrode and extending from the second electrode within the tube and said apparatus is no larger radially at either of said first and second electrodes than at any region between said electrodes.

9. An apparatus as defined in claim 1 wherein said lead is welded to the electrode and the weld is in said lumen and faces generally away from the opening.

10. An apparatus for making electrical contact within the heart of a patient comprising:
an elongated tube sized to pass through a vein or an artery and into the heart, said tube having proximal and distal ends, a peripheral wall, at least one lumen extending longitudinally within the tube and an opening in the peripheral wall which extends from the lumen to the exterior of the tube;
an electrode;
means at least partially within the lumen for mounting the electrode within said lumen with the electrode being exposed at said opening;
at least one conductive lead coupled to said electrode and extending from said electrode within said tube; and said electrode including a tubular conductive member having a passage extending generally axially therethrough, said mounting means including a mounting member extending completely through said passage and having end portions outside said passage on opposite sides of the conductive member, at least a portion of said end portions lying in said lumen on opposite sides of the opening to at least assist in mechanically locking the conductive member within the lumen, an insulating adhesive to at least assist in bonding the conductive member and the mounting member together and in retaining them within the lumen.

11. An apparatus as defined in claim 10 wherein said tube has a body line and said electrode extends radially outwardly no farther than said body line.

12. An apparatus as defined in claim 10 wherein said lead is welded to the electrode, the weld is in said lumen and faces generally away from the opening.

13. An apparatus as defined in claim 10 wherein the mounting member is resilient and bendable.

14. An apparatus for making electrical contact within the heart of a patient comprising:
   an elongated tube sized to pass through a vein or an artery and into the heart, said tube having proximal and distal ends, a peripheral wall, at least one lumen extending longitudinally within the tube and an opening in the peripheral wall which extends from the lumen to the exterior of the tube;
   a tubular electrode;
   a mounting member at least partially within the lumen and the tubular electrode mounting the electrode within said lumen with the electrode being exposed at said opening;
   an insulating adhesive holding the mounting member and the electrode together, said insulating adhesive partially circumscribing the electrode and leaving a region of the electrode exposed at said opening; and
   at least one conductive lead coupled to said electrode at a location out of said region and extending from said electrode within said tube and at least partly through the adhesive.

15. An apparatus as defined in claim 14 wherein said mounting member extends completely through the tubular electrode and has end portions on opposite sides of the tubular electrode.

16. An apparatus for making electrical contact within the heart of a patient comprising:
   an elongated tube sized to pass through a vein or an artery and into the heart, said tube having proximal and distal ends, a peripheral wall, at least one lumen extending longitudinally within the tube and an opening in the peripheral wall which extends from the lumen to the exterior of the tube;
   an electrode including a conductive member with a generally axial passage;
   means at least partially within the lumen for mounting the electrode within said lumen with the electrode being exposed at said opening, said mounting means including a mounting member in said lumen, at least a portion of said mounting member being in said passage, extending into said lumen and being displaced axially of the opening to at least assist in mechanically locking the conductive member in the lumen;
   at least one conductive lead coupled to said electrode and extending from said electrode within said tube;
   said peripheral wall having an outer peripheral surface which extends along said tube with the outline of said peripheral surface over said opening forming a body line and said electrode extends radially outwardly no farther than said body line whereby said apparatus is no larger radially at the electrode than at regions lying axially of the electrode and the mounting means; and
   said passage extending through said electrode and said mounting means extending through said passage and having end portions outside said passage on opposite sides of the conductive member.

* * * * *